US 7,445,934 B2
Nov. 4, 2008

United States Patent
DiFoggio et al.

(54) SYSTEM AND METHOD FOR ESTIMATING FILTRATE CONTAMINATION IN FORMATION FLUID SAMPLES USING REFRACTIVE INDEX

(75) Inventors: Rocco DiFoggio, Houston, TX (US); Angus Simpson, Cypress, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 11/696,537

(22) Filed: Apr. 4, 2007

(65) Prior Publication Data

US 2007/0238180 A1    Oct. 11, 2007

Related U.S. Application Data

(60) Provisional application No. 60/790,657, filed on Apr. 10, 2006.

(51) Int. Cl.
*G01N 33/26* (2006.01)
*G01N 21/41* (2006.01)
*E21B 49/10* (2006.01)

(52) U.S. Cl. ............................ 436/29; 166/66; 166/100; 166/250.03; 166/264; 356/128; 436/28; 436/30; 436/139; 436/164

(58) Field of Classification Search .................. 166/66, 166/100, 250.03, 264; 356/128; 436/28–30, 436/139–142, 164
See application file for complete search history.

(56) References Cited

U.S. PATENT DOCUMENTS

| | | | | |
|---|---|---|---|---|
| 5,831,743 | A * | 11/1998 | Ramos et al. | 356/445 |
| 6,016,191 | A * | 1/2000 | Ramos et al. | 356/70 |
| 6,023,340 | A * | 2/2000 | Wu et al. | 356/432 |
| 6,075,611 | A * | 6/2000 | Dussan V. et al. | 356/432 |
| 6,683,681 | B2 | 1/2004 | DiFoggio et al. | |
| 6,729,400 | B2 | 5/2004 | Mullins et al. | |
| 6,927,846 | B2 * | 8/2005 | Smith et al. | 356/128 |
| 6,997,055 | B2 | 2/2006 | DiFoggio | |
| 7,016,026 | B2 | 3/2006 | DiFoggio et al. | |
| 2002/0023780 | A1 | 2/2002 | Skinner | |
| 2002/0084072 | A1 | 7/2002 | Bolze et al. | |
| 2002/0112854 | A1 | 8/2002 | Krueger et al. | |
| 2003/0112427 | A1 | 6/2003 | Ryan et al. | |
| 2003/0145988 | A1 | 8/2003 | Mullins et al. | |
| 2003/0193662 | A1 | 10/2003 | DiFoggio et al. | |
| 2003/0206290 | A1 | 11/2003 | Byrne et al. | |
| 2003/0226663 | A1 | 12/2003 | Krueger et al. | |

(Continued)

OTHER PUBLICATIONS

Pham, D. T.-K, et al, Journal of Petroleum Science & Engineering 1998, 20, 239-246.*

(Continued)

*Primary Examiner*—Arlen Soderquist
(74) *Attorney, Agent, or Firm*—Madan Mossman and and Sriram PC

(57) ABSTRACT

A method and apparatus is described for estimating terminal purity or terminal contamination for a fluid during the withdrawal of the fluid from a subsurface formation. The apparatus and method provide for measuring refractive index of the fluid over a time period, fitting a curve through the refractive index measurements or data values derived therefrom and estimating a terminal refractive index or terminal value for the data values from the fitted to curve to estimate the terminal contamination or purity for the fluid.

25 Claims, 5 Drawing Sheets

U.S. PATENT DOCUMENTS

| | | |
|---|---|---|
| 2004/0000400 A1 | 1/2004 | Fujisawa et al. |
| 2004/0075827 A1 | 4/2004 | Byrne |
| 2004/0099443 A1 | 5/2004 | Meister et al. |
| 2004/0109156 A1 | 6/2004 | DiFoggio et al. |
| 2004/0125363 A1 | 7/2004 | Langenbacher et al. |
| 2004/0130706 A1 | 7/2004 | Frot |
| 2004/0139798 A1 | 7/2004 | Haddad et al. |
| 2004/0173351 A1 | 9/2004 | Fox et al. |
| 2004/0189982 A1 | 9/2004 | Galarneau et al. |
| 2004/0238220 A1 | 12/2004 | Meister et al. |
| 2005/0110982 A1 | 5/2005 | Larkin |
| 2005/0205256 A1 | 9/2005 | DiFoggio |
| 2005/0213080 A1 | 9/2005 | Huang et al. |
| 2006/0000606 A1 | 1/2006 | Fields et al. |
| 2006/0042793 A1 | 3/2006 | Del Campo et al. |
| 2006/0076132 A1 | 4/2006 | Nold et al. |
| 2006/0090894 A1 | 5/2006 | Seeberg-Elverfeld et al. |
| 2006/0137873 A1 | 6/2006 | Caudwell et al. |
| 2006/0180302 A1 | 8/2006 | Intelisano |
| 2007/0007005 A1 | 1/2007 | Heller et al. |
| 2007/0039731 A1 | 2/2007 | Fox et al. |
| 2007/0079962 A1 | 4/2007 | Zazovsky et al. |
| 2007/0097356 A1 | 5/2007 | Stumpe et al. |
| 2007/0114021 A1 | 5/2007 | Brown et al. |
| 2007/0205021 A1 | 9/2007 | Pelletier et al. |
| 2007/0209793 A1 | 9/2007 | Nold et al. |
| 2007/0215348 A1 | 9/2007 | Corre et al. |
| 2007/0215349 A1 | 9/2007 | Reid et al. |

OTHER PUBLICATIONS

The International Association for the Properties of Water and Steam; Erlangen, Germany; Sep. 1997; Release on the Refractive Index of Ordinary Water Substance as a Function of Wavelength, Temperature and Pressure.

Proc. Indian Acad. Sci. (Chem, Sct.), vol. 115, No. 2, Apr. 2003, pp. 147-154; Indian Academy of Sciences; Application of Refractive Index Mixing Rules in Binary Systems of Hexadecane and Heptadecane with n-alkanols at different temperatures.

* cited by examiner

SYSTEM AND METHOD FOR ESTIMATING FILTRATE CONTAMINATION IN FORMATION FLUID SAMPLES USING REFRACTIVE INDEX

CROSS-REFERENCE TO RELATED APPLICATIONS

This application takes priority from U.S. Provisional Patent Application Ser. No. 60/790,657 filed Apr. 10, 2006.

BACKGROUND OF THE DISCLOSURE

1. Field of the Disclosure

This disclosure relates to an apparatus and a method for estimating a condition of formation fluid using an index of refraction during withdrawal of such fluid from the formation.

2. Description of the Related Art

Oil and gas wells are drilled while circulating drilling fluid (also referred to as "mud") in the wellbore. Drilling fluids are typically water-based or oil-based. After drilling the well and before completing the well for the production of hydrocarbons, fluid samples are often withdrawn from the subsurface formation at various wellbore depths to determine the characteristics of the fluid in order to determine the location and fraction or amount of hydrocarbons in the formation fluid and the condition of the reservoirs, etc. In some cases, it also is desirable to obtain samples from the formations or zones that contain mostly formation brine, i.e., water samples.

A majority of the wells are drilled under overbalanced conditions, that is, the wells are drilled wherein the pressure in the wellbore due to the weight of the drilling fluid is greater than the formation pressure. The drilling fluid invades or penetrates to varying depths in the formation, depending upon the physical conditions of the formation being drilled, such as porosity, permeability and other rock properties. This fluid penetration (also referred to as the fluid invasion) contaminates the connate or virgin fluid in the formation. Therefore, before obtaining a fluid sample downhole, a tool is set at the desired depth and the fluid is withdrawn or pumped from the formation into the wellbore until it is determined that the fluid being withdrawn is substantially free of the drilling fluid. Downhole tools referred to as "formation testers" are typically set at the desired depth in the wellbore to pump out the fluid and to withdraw the formation fluid samples. Initially, fluids that are withdrawn from the formation are often highly contaminated with filtrates of the drilling fluid used for drilling the wellbore. To obtain samples that are sufficiently clean (usually <10% contamination) formation fluids are generally pumped from the formation into the wellbore for a period of time, typically 30-90 minutes, before collecting samples in sample chambers for laboratory analysis. Optical sensors are often used to monitor a contamination level in the withdrawn fluid. Optical absorption measurements have been used to estimate how long it might take before relatively clean fluid samples can be taken and to estimate the eventual purity or contamination levels if the fluid is pumped for a relatively long time period. Refractive index measurements have been taken downhole but have not been used to estimate purity or contamination levels for brine. Refractive index measurements can be much less sensitive to the passage of sand particles or other elements present in the formation fluid that may scatter light in the fluid being analyzed than optical absorption spectral measurements.

Therefore, it is desirable to provide an apparatus and method that uses refractive index measurements to estimate one or more characteristics of brine obtained from formations that have water-based invasion, to determine purity or contamination of brine while withdrawing the fluid from a formation, and to estimate at a given time how long it might take before clean up will occur so that a sample may be taken. In certain situations, such as when the invaded zone is too deep or when there is continued penetration of an unwanted fluid from adjacent formations during the pumping of the fluid, it may not be feasible to obtain a clean sample even if pumping were to continue for a relatively long time period. In such cases it is desirable to determine in a relatively short time that it may not be feasible to withdraw samples in a reasonable amount of time from the particular location in the wellbore.

SUMMARY OF THE DISCLOSURE

In one aspect, a method for estimating a characteristic of brine present in the fluid obtained from a formation that has water-based mud invasion is disclosed. The method includes: estimating a refractive index of the connate brine from well log measurements; withdrawing the fluid from the formation; measuring a refractive index of the fluid a plurality of times during the withdrawal of the fluid from the formation; estimating the characteristic of the brine by comparing the estimated refractive index of the connate brine with a refractive index measured during the withdrawal of the formation.

In another aspect, a method for estimating a characteristic of brine in a fluid obtained from a formation that has water-based mud invasion is provided wherein the method includes: estimating a refractive index of the connate brine from well log data; withdrawing the fluid from the formation; measuring a refractive index of the fluid a plurality of times during the withdrawal of the fluid; fitting a curve to data values that correspond to the plurality of refractive index measurements; and estimating the characteristic of the brine from the estimated refractive index of the connate brine and the fitted curve.

In another aspect, a method for estimating a characteristic of a fluid obtained from a formation is provided, wherein the method includes: withdrawing the fluid from a formation; measuring a refractive index of the fluid during the withdrawal of the formation fluid to obtain a plurality of refractive index values; obtaining a plurality of resistivity values corresponding to the plurality of refractive index values; fitting a curve through the plurality of resistivity values; estimating a terminal value of the resistivity values from the fitted curve; and estimating the characteristic of the fluid using a current resistivity value and the estimated terminal value.

In another aspect, an apparatus for estimating a characteristic of brine in a fluid withdrawn from a formation is disclosed that includes a probe to withdraw the fluid from the formation; a refractometer that provides refractive index measurements of the fluid during the withdrawal of the fluid from the formation; and a storage device that has stored therein an estimated value of refractive index of connate brine in the formation that is obtained using well log data; and a processor that estimates the characteristic of the brine from the estimated value of the refractive index of the connate brine and refractive index measurements made during the withdrawal of the fluid from the formation.

In another aspect, the apparatus includes a probe to withdraw the fluid from the formation; a refractometer that provides a plurality of refractive index measurements of the fluid during the withdrawal of the fluid from the formation; a storage device that has stored therein an estimated value of refractive index obtained from well log data; and a processor that: fits a curve to data values that correspond to the plurality of refractive index measurements; and estimates the characteristic of the brine in the withdrawn fluid from the estimated refractive index and the fitted curve.

Examples of the more important features of the apparatus and method disclosed herein have been summarized rather broadly in order that the detailed description thereof that follows may be better understood, and in order that the contributions to the art may be appreciated. There are, of course, additional features of the invention that will be described hereinafter and which will form the subject of the claims.

BRIEF DESCRIPTION OF THE DRAWINGS

For a detailed understanding of the apparatus and methods described herein, references should be made to the following detailed description of the embodiments, taken in conjunction with the accompanying drawings, in which like elements have been given like numerals, wherein.

DETAILED DESCRIPTION OF THE EMBODIMENTS

Figure 1:
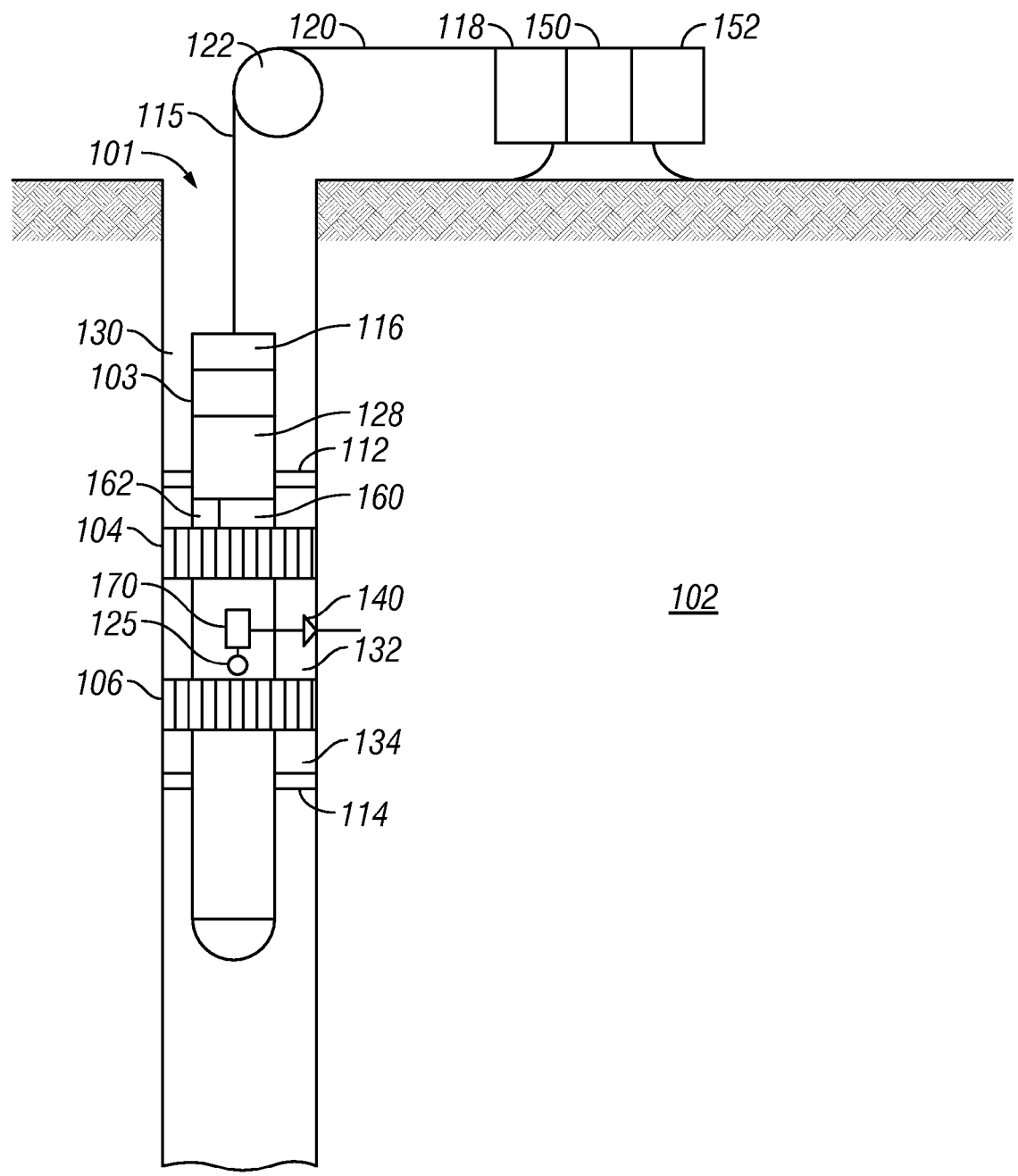
FIG. 1 is an elevation view of a wireline system according to one embodiment of the present disclosure.

FIG. 1 shows a schematic diagram of a wireline system according to one embodiment of the present disclosure. A well 101 is shown traversing a formation 102. A wireline tool 103 supported by an armored cable 115 is disposed in the well 101 adjacent the formation 102. Extending from the tool 103 are optional grippers 112 and 114 for stabilizing the tool 103. Two expandable packers 104 and 106 disposed on the tool 103 are capable of separating the annulus of the borehole 101 into an upper annulus 130, a sealed intermediate annulus 132 and a lower annulus 134. A selectively extendable pad member 140 is disposed on the tool 103. The grippers 112, packers 104 and 106, and extendable pad element 140 are used to withdraw the fluid and are described in more detail in reference to FIG. 2.

Telemetry for the wireline embodiment includes a downhole two-way communication unit 116 connected to a surface two-way communication unit 118 by one or more conductors 120 within the armored cable 115. The surface communication unit 118 is housed within a surface controller 150 that includes a processor, memory and an output device, collectively designated by numeral 152. A typical cable sheave 122 is used to guide the armored cable 115 into the borehole 101. The tool 103 includes a downhole controller 160 having a processor and memory 162 for controlling formation tests in accordance with methods described herein. The downhole tool 103 includes a plurality of sensors including an optical sensing module 170 and optional sample tanks 128. The optical sensing module 170 is used to measure refractive index of the fluid withdrawn from the formation over time at selected locations and at varying depths within the borehole 101. The tool 103 also included other sensors (generally denoted by number 125), such as pressure sensor, temperature sensor, flow meter, etc.

Figure 2:
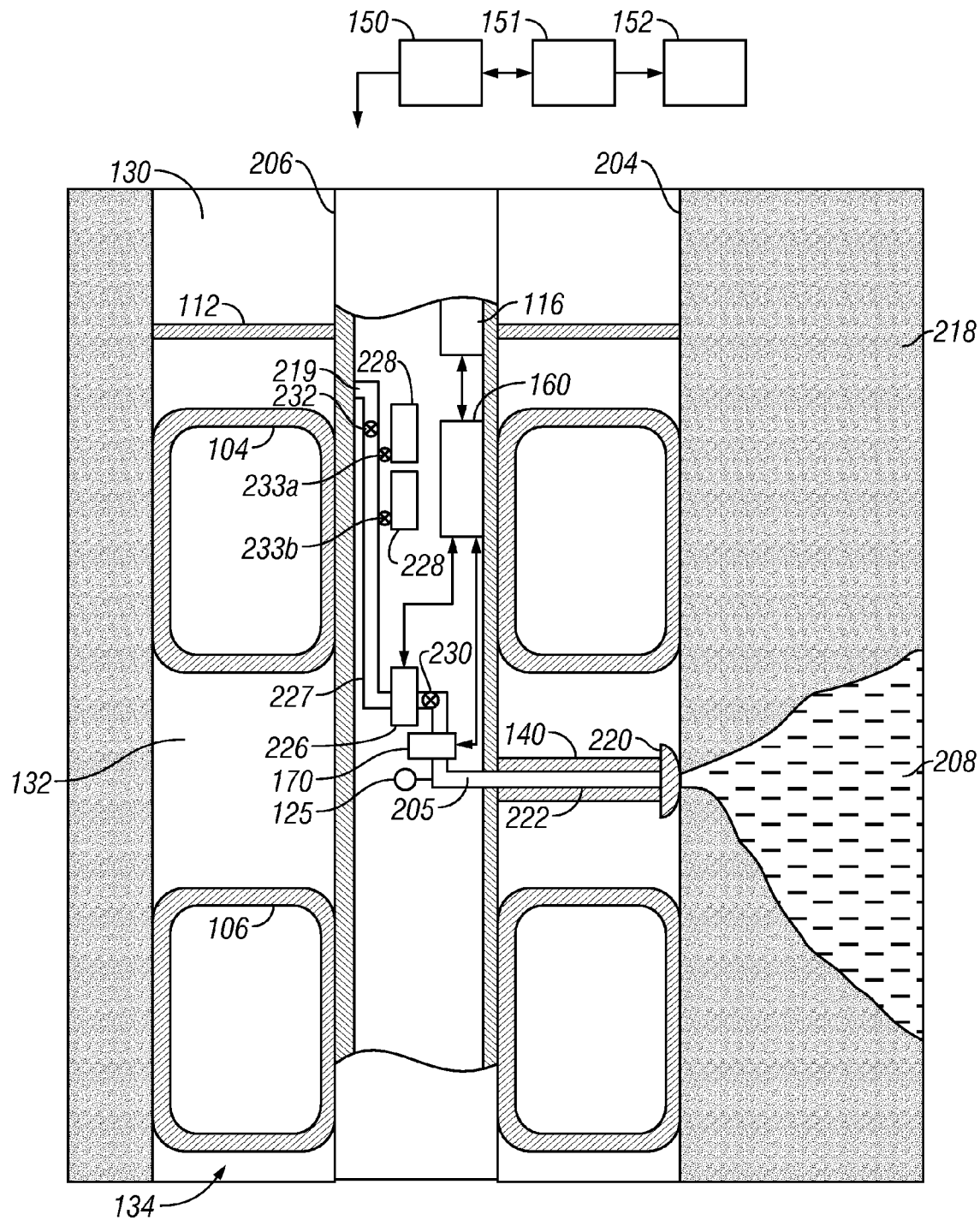
FIG. 2 is a schematic diagram of a formation testing tool for use in the system of FIG. 1 according to one embodiment of the present disclosure.

FIG. 2 shows a schematic diagram of a portion of a formation testing tool 103 deployed in a wellbore for withdrawing the fluid from the formation and for taking refractive index measurements in-situ. Selectively extendable gripper elements 112 engage the borehole wall 204 to anchor a tubular member 206 of the tool 103. Packer elements 104 and 106 extend to engage the borehole wall 204. The extended packers separate the well annulus into three sections, an upper annulus 130, an intermediate annulus 132 and a lower annulus 134. The sealed annular section (or sealed section) 132 is adjacent a formation 218. Mounted on the tubular member 206 and extendable into the sealed section 132 is a selectively extendable pad sealing element 140. A fluid line 222 providing fluid communication between formation fluid 208 and tool sensors, such as optical sensing module 170, is shown extending through the pad member 140 to provide a sealed port 220 against the wall 204. In addition, sensors 125 are included for determining pressure, temperature and flow rate of the formation fluid sample. Packers 104 and 106 sealingly urge against the wall 204 and have a sealed relationship between the wall 204 and extendable element 140. Reducing the pressure in the sealed section 132 prior to engaging the pad 140 initiates fluid flow from the formation into the sealed section 132. When the extendable element 140 engages the wall, the fluid 208 from the formation flows into the tool via the 220. The extendable element 140 is set along a particular orientation. A sensor, such as an accelerometer, may be used to sense the orientation of the extendable element 140. The extendable element 140 may then be oriented to the desired direction.

A downhole controller 160 controls the withdrawal of the formation fluid 208. The controller 160 is connected to a system volume control device, such as pump 226. The pump 226 may be a progressive cavity pump or any suitable pump that can pump out formation fluid 208 from the formation 218. A flow meter is included to determine the fluid flow rate. A valve 230 for controlling fluid flow to the pump 226 is disposed in the fluid line 222 between the optical sensing module 170 and the pump 226. A test volume 205 is the volume below the retracting piston of the pump 226 and includes the fluid line 222.

The optical sensing module 170 is used to determine the refractive index of the formation fluid within the test volume 205. Any suitable optical module or system for determining the refractive index may be used. In one aspect, the optical sensing module is configured to measure the refractive index using reflection-intensity at a window-fluid interface. The refractive index is computed by comparing the reflection intensity of an air filled cell to the reduced reflection intensity when some other fluid is in the cell and using the known refractive indices of the window (typically a sapphire window) and of air. The refractometer of the optical sensing module 170, in one aspect, may be configured to measure refractive index in-situ of any desired fluid, including that of oil, gas and brine. The refractometer may have a broad range, such as from n=1.0 to n=1.75, and a relatively high resolution, such as 0.00025 or better. Such a refractometer provides a relatively broad refractive index range and has a relatively high resolution. Such a refractometer provides refractive index measurements that are useful for monitoring sample cleanup from mostly mud filtrate to mostly pure or connate formation fluid described herein. Any suitable refractometer may be used for the purpose of this disclosure, including but not limited to those described in U.S. Pat. No. 6,683,681 B2 and U.S. Published Application 2004/0007665 A1, each of which is assigned to the assignee of this application, and each of which is incorporated herein by reference.

The optical sensing module 170 is connected to the controller 160 to provide the feedback data for a closed-loop control system. The feedback is used to adjust parameter settings such as detecting sample clean-up. Sample clean up refers to the transition from filtrate-contaminated formation fluid to connate or nearly pure formation fluid while pumping fluid at selected depths in the wellbore. The downhole controller 160 may incorporate a processor, such as a microprocessor, for processing the reflective index measurements. A storage device, such as a memory device, may be used as a computer-readable medium to store data, computer programs and algorithms relating to the use by the apparatus described herein and to perform the various functions and methods relating to such apparatus.

During the clean-up process, the withdrawn fluid is vented to the upper annulus 130 via line 219. A conduit 227 connecting the pump 226 to the line 219 includes a selectable internal valve 232. If fluid sampling is desired, the fluid may be diverted to optional sample reservoirs or tanks 228 by using the internal valves 232, 233a, and 233b rather than venting the fluid through the line 219. The fluid contained in the reservoirs 228 is retrieved from the well for analysis.

In one aspect, the results of the data processed downhole may be sent to the surface for use and for further processing. The controller 160 passes the processed data to a two-way data communication system 116 disposed downhole. The communication system 116 transmits a data signal to a surface controller 150, which controller contains a processor 151 and memory storage device that stores computer programs, algorithms and data for use in the apparatus and methods described herein. Any suitable data communication system may be used for the purpose of this disclosure. The signals received at the surface are processed by the processor 151 associated with the surface controller 150, which converts and transfers the data to a suitable output and/or storage device 152. The surface controller 150 may also be used to send the test initiation commands to the downhole tool 103.

Figure 3:
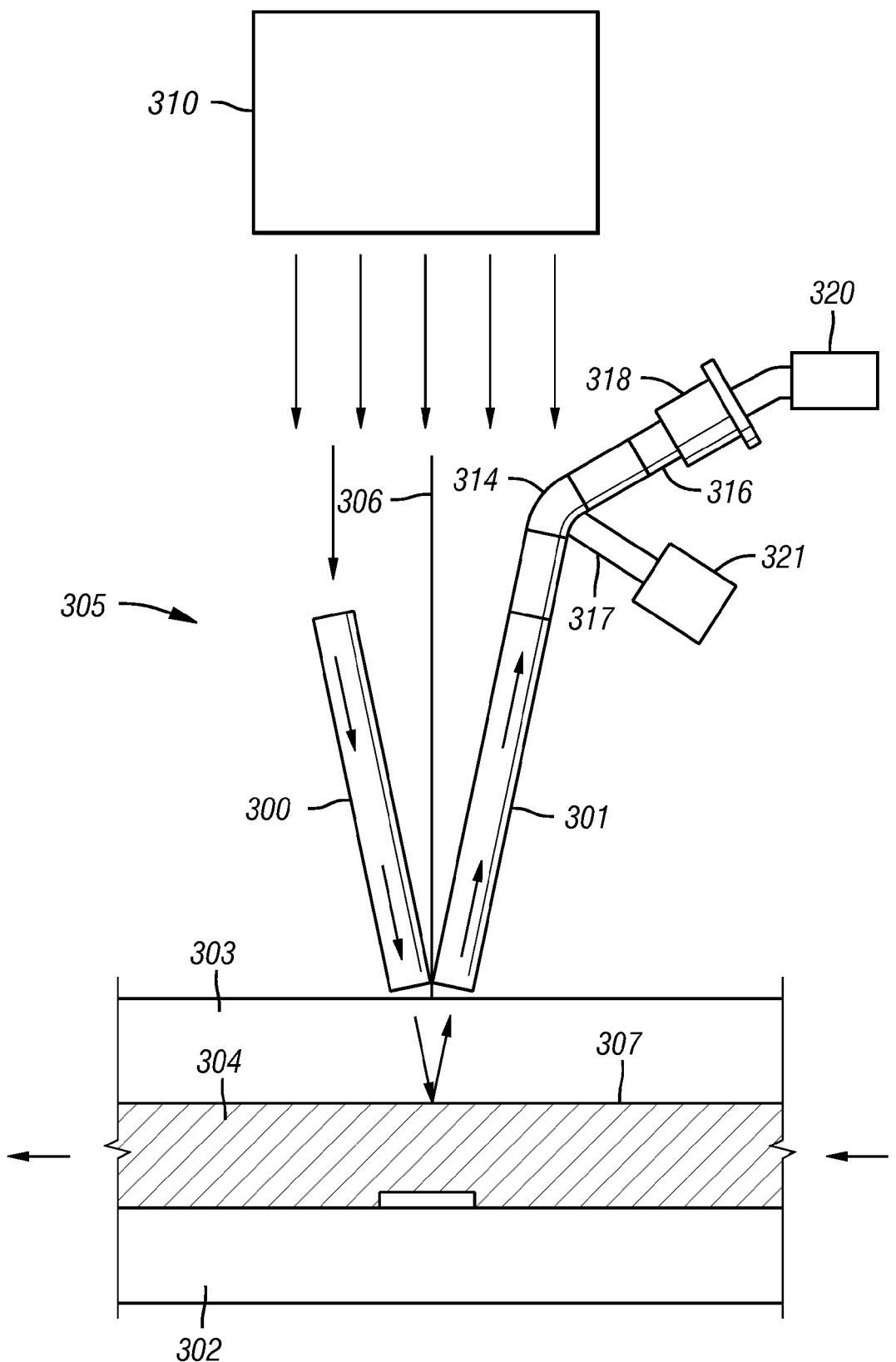
FIG. 3 is a schematic of an optical refractometer suitable for use in a downhole tool of FIG. 2 for determining refractive index of fluid samples.

FIG. 3 shows a schematic of a refractometer assembly 305 for use in the optical sensing module 170. A light source 310 comprising a light bulb and a collimitor lens provides collimated light beam. The collimated light beam, in aspect, may be incident substantially perpendicular to the exterior surface of a first sapphire window 303. The light after interaction with the fluid exits from a second sapphire window 302. Sapphire windows 303 and 302, in one configuration may lie substantially perpendicular to the collimated beam of light and separated by a gap or channel 304, enabling formation fluid under analysis to flow between the windows. In one embodiment, the refractometer assembly 305 diverts a portion of the incident collimated beam from source 310 and focuses it onto interface 307 between the first sapphire window 303 and the fluid in channel 304. The reflected light beam is split at beam splitter 317 between a refractometer (316, 318, and 320) and an attenuated reflectance spectrometer 621. The portion of the collimated light beam that is not diverted for use in the refractometer or the attenuated reflectance spectrometer, continues on for use in other sensors.

FIG. 3 shows two optical transmission rods 300, 301 (which may be relay lenses, glass or sapphire rods) which are also referred to as the left rod 300 and the right rod 301 may be used for guiding light. In one configuration, the longitudinal axes of the two optical transmission rods lie in a plane perpendicular to the plane of both of the pressure containment plates comprising a first sapphire window 303 and a second sapphire window 302 and the channel 304. In addition, the two optical transmission rods 300, 301 may be placed side-by-side (and contacting each other where they meet at surface 303) and may also be in contact with the first sapphire plate 303. To maximize the light signal, a high-temperature index matching gel may be applied to bridge the gap between transmission rods 300, 301 and first sapphire plate 303. Leaving the gap unfilled except for air does not change the refractive index measurement because it diminishes the light intensity measurements of both the unknown and the reference sample by the same factor. Such a system may be used to determine the refractive index of the formation fluid sample in channel 304 (FIG. 2). Details of the measurement and analysis techniques for determining the refractive index, are provided in U.S. Pat. No. 6,683,681 B2 and U.S. Published Application 2004/0007665 A1, which are incorporated herein by reference.

Figure 4:
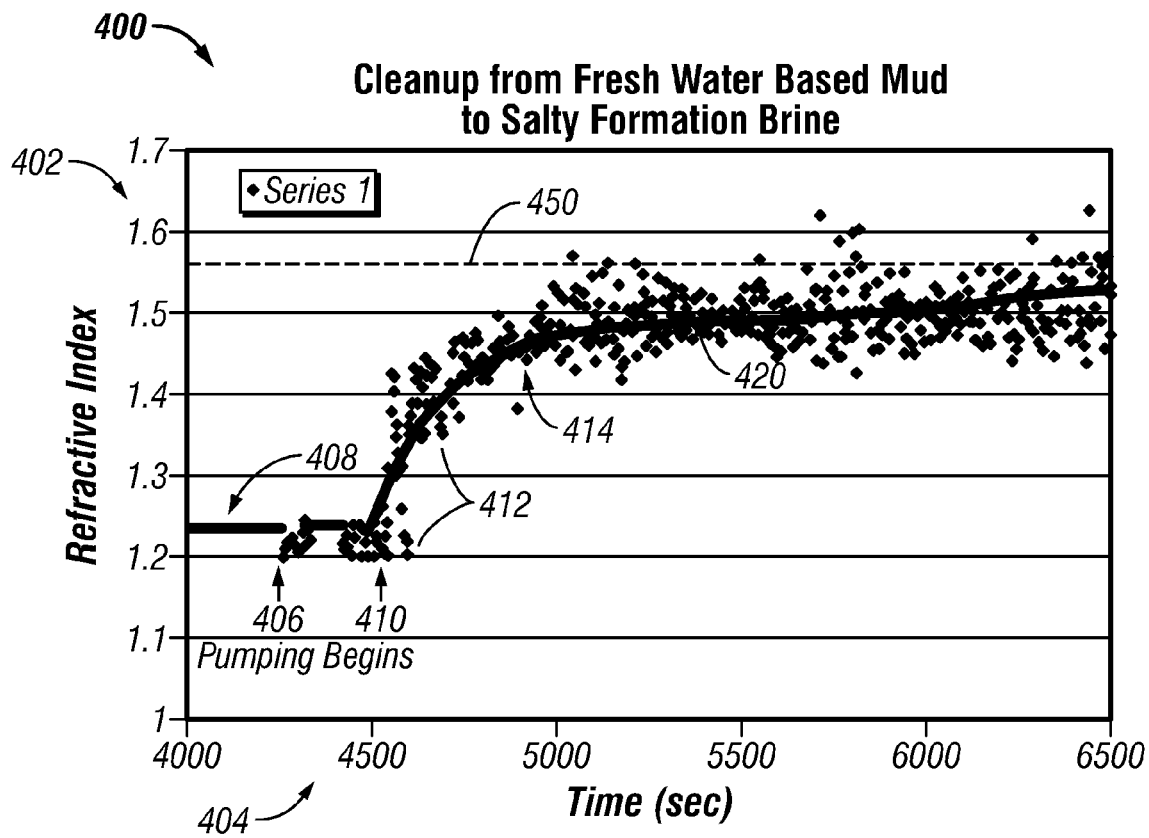
FIG. 4 is a graph showing an example of refractive index measurements taken over a time period when the fluid withdrawn from a formation changes from water-based mud filtrate to mostly formation brine.

FIG. 4 is a graph 400 showing an example of in-situ measurements of refractive index taken over selected time period during pumping of a fluid from the formation. In the particular example of FIG. 4, the drilling fluid used is water-based mud and the connate fluid is formation brine. The refractive index is shown along the y-axis 402 and the time is shown along the x-axis 404. During the time period until the pumping begins at time 406 (about 4200 seconds) the refractive index taken by the refractometer of the kind shown and described with respect to FIG. 3 shows a very stable and constant value, as indicated by constant value 408. As pumping starts, the refractive index of the fluid being withdrawn changes and after a short period of time, starting at time indicated by arrow 410, starts to increase. As the fluid is pumped, the proportion of the filtrate (mud) in the fluid starts to decrease and that of the connate fluid starts to increase. In other words, as the fluid is pumped from the formation, the fluid undergoes a cleaning up process in which the purity of the sample increases as the filtrate is removed from the invaded zone of the formation. Thus, the fraction of the connate fluid or the fraction of purity "fp" starts to increase while the fraction of the contamination "fc" starts to decrease. In the particular example of FIG. 4, the drilling fluid is water-based mud and the connate fluid is formation brine. Because the refractive index of water-based mud is lower than the refractive index of formation brine, the refractive index of the withdrawn fluid increases over time. This is because the density (and refractive index) of the water-based mud is less than the density of the formation brine. As shown in FIG. 4, the refractive index rises rapidly up to time indicated by arrow 414 and then starts to taper off, i.e., starts to increase relatively slowly over time. In the particular example of FIG. 4, the refractive index is shown to increase until the time of about 6500 seconds. Typically, at long pumping times (which may be 24 hours, etc.), a dynamic equilibrium is reached in which the fluid sample being withdrawn from the formation cleans up at the same rate as it is re-contaminated from adjacent zones, such as the zones above and below the zone from where the sample is being taken. Thus, often, even though the downhole measurement, such as the refractive index, has substantially stopped changing, the sample still not is at 100% purity. The dynamic equilibrium depends on various factors, such as the ratio of the vertical to horizontal permeability. For the purpose of this disclosure, the purity level that may be achieved after a very long period of time is referred to as the terminal purity, ftp, which is usually less than 100%. The corresponding terminal contamination (1-ftp) is designated as "ftc." Thus, it is desirable to estimate by monitoring the measurement how long it might take to achieve the terminal purity or the corresponding terminal contamination. Also, while extracting the fluid from the formation, it is desirable to estimate the actual clean-up, i.e., the degree of contamination or purity in real time. If the amount of filtrate at the terminal purity is greater than a certain selected amount (for example, greater than 5% or 10%), it may not be desirable to take any sample at the selected location in the wellbore and that it may be more desirable to terminate the fluid extraction process and move the tool to a different location in the wellbore.

Still referring to FIG. 4, line 450 indicates an estimated or computed value of the refractive index of the connate brine. A comparison of the estimated connate brine refractive index and the measured refractive index of the contaminated mixture provides the fraction of connate brine in the fluid mixture being withdrawn. The contamination level or the purity level may be computed from a comparison of the two refractive indices. In one aspect, the estimated value of the refractive index of the connate brine may be computed from prior data and knowledge of the rock properties of the formation from where the fluid is being withdrawn. The refractive index of the mud filtrate can be measured directly. Alternatively, it can be estimated from other properties such as resistivity in the case of water based muds. The comparisons made may include computing differences and using ratios of selected measurements or values.

In one aspect, when collecting a water sample in a well drilled with water-based mud, well logs may be used to estimate the connate brine's resistivity and, from that, the connate brine's refractive index. As an example, the brine resistivity nay be estimated by using typical rock properties for the region of the wellbore, such as Archie parameters "a" and "m" of the resistivity factor (F=a/Porosity ^m) along with the deep-reading resistivity logs and neutron porosity logs over the water zone. Similarly, neutron logs may be used to estimate brine salinity. For a zone that is 100% saturated with water, the log-measured neutron cross-section equals Sigma_Log=Sigma_Brine*Porosity+Sigma_Matrix*(1−Porosity). From the effect of the dissolved salt on the brine's cross-section, brine salinity may be obtained by solving for Sigma_Brine in terms of typical neutron cross-sections for the formation of interest and the porosity as measured by neutron logs. Then from the brine resistivity and the pressure and temperature, brine's refractive index may be computed. The relationship between resistivity, pressure, temperature, and refractive index are discussed in U.S. Pat. No. 7,027,928. By either directly measuring the water-based mud filtrate's refractive index or by knowing its resistivity and then computing its refractive index, both end points from which to compute the percentage of contamination become known. That is, the refractive index of both the pure water-based mud filtrate (one endpoint) and the pure formation brine (the other endpoint) become known. The fraction of contamination may be computed as a linear interpolation between the two pure fluid endpoints.

When collecting an oil sample for a well drilled with oil-based mud, prior knowledge of produced fluid in the region to estimate the formation crude oil's refractive index may be used. If the oil based mud filtrate's refractive index is directly measured, then both end points are known from which the fraction of contamination may be obtained from a linear interpolation between the pure fluid endpoints.

Still referring to FIG. 4, at any time during the withdrawal of the fluid, the refractive index of the fluid is known. By comparing a current value of the refractive index and the estimated value of line 450, the contamination or purity levels can be obtained. If the difference between the estimated value of line 450 and the terminal value of the data in FIG. 4 (described in more detail later) is greater than a selected value, then it may not be feasible to obtain a relatively clean sample even if the fluid is pumped from the formation for extended time period. In such a situation, the tool may be moved to different location in the wellbore for obtaining clean samples. The system, apparatus and methods described herein may be configured to provide both qualitative and quantitative measures of the current and terminal purity and contamination levels using a set of refractive index measurements taken over a selected time period. In one aspect, the present disclosure provides an indication or estimate in real time of the fraction of the pumping-time that has passed before formation fluid purity will reach a certain level from the changes in the refractive index. For example, the difference between the refractive index of highly-saline formation brine and that of a fairly fresh water-based mud is approximately 0.030. Thus, from the current refractive index and the estimated terminal refractive index or the estimated connate brine refractive index, the system of the present disclosure can estimate the fraction of the contamination or the clean fluid in real time.

In another aspect, the system of the present invention provides an estimate of the terminal purity or the contamination level by fitting a suitable curve to the refractive index data taken over a selected time period. For the purpose of this invention, any suitable curve fitting technique or algorithm may be used. Certain examples of curve fitting techniques that may be used for this invention are described later. A curve that may be fitted to the data of FIG. 4 is shown as the solid line 420.

Figure 5:
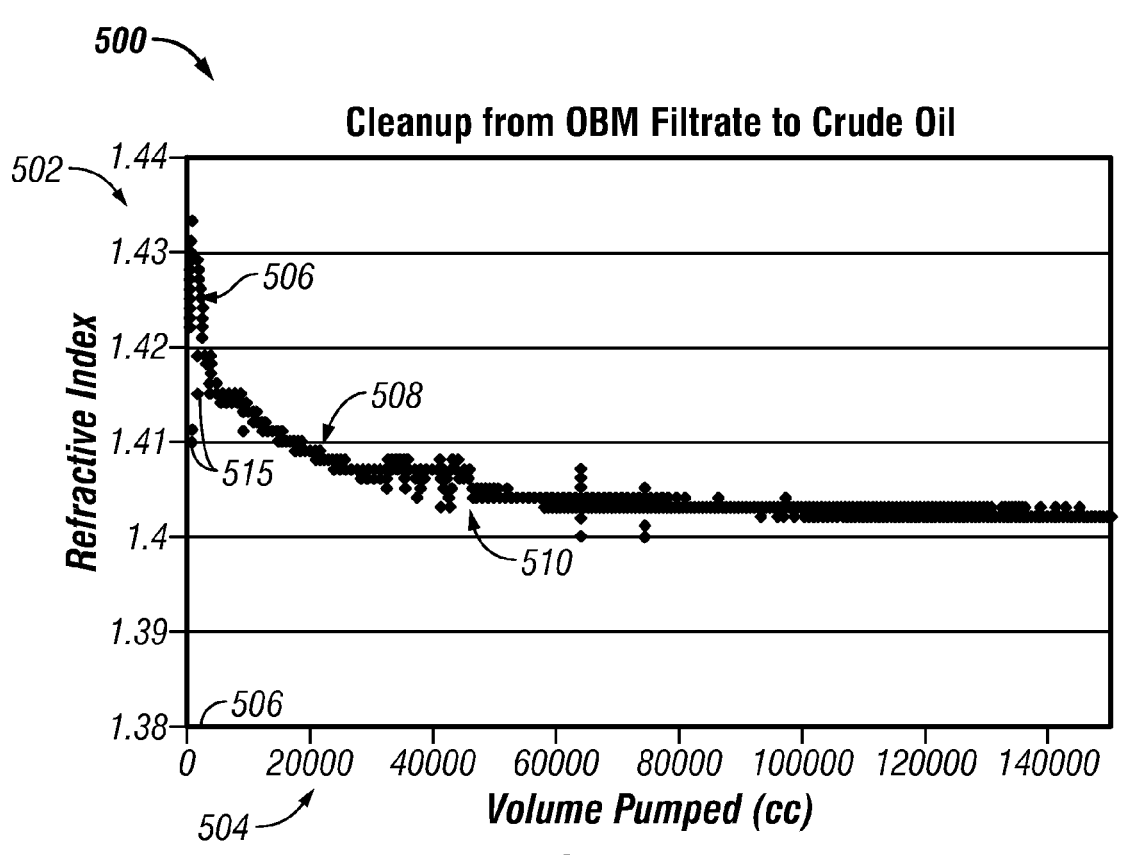
FIG. 5 is a graph showing an example of refractive index measurements taken over a time period when the withdrawn fluid changes from oil-based mud filtrate to mostly formation crude oil.

FIG. 5 is a graph showing an example of in-situ measurements of refractive index taken over a selected time period during pumping of the fluid from the formation wherein the drilling fluid used is an oil-based mud and the connate fluid is crude oil. The refractive index (rounded to the nearest 0.001) is shown on the y-axis 502 and the volume of the fluid pumped is shown along the x-axis 504. The example of FIG. 5 uses the volume pumped instead of the time used in FIG. 4. In certain cases, fluid volume pumped may be a more appropriate parameter, for example when the fluid pump rate is not substantially constant over the pumping time period. When the pumping begins at volume zero (506), the refractive index measured by the refractometer of the kind shown and described with respect to FIG. 3 shows certain erratic measurements, such as indicated by numeral 515. Such measurements can occur due the erratic changes in the composition of the initial fluid pumped. As the volume pumped increases, the refractive index of the fluid beings to drop rapidly as shown by the initial part of the data generally represented by arrow 506 and then starts to decrease more gradually as shown by the data generally represented by arrow 508. For any particular pumping, the rate of change of the refractive index depends on the amount of the clean-up. In the particular example of FIG. 5, as the pumping continues from the volume indicated by arrow 510 (between 4000-5000 cc), the refractive index starts to decrease relatively slowly. In the particular example of FIG. 5, the dynamic equilibrium or the terminal purity may be achieved beyond a much greater pumping volume, shown here to be beyond the volume of 14000 cc.

In the example of FIG. 5, the refractive index decreases as the fluid is pumped because the refractive index of oil-based mud is greater than that of the crude oil. The system of the present invention fits a suitable curve to the data and provides an estimate of the refractive index at terminal purity and the current purity (or contamination) of the withdrawn fluid. When the refractive index of the filtrate and pure formation fluid are known, the percentage of purity or contamination can be determined by linear interpolation between these two endpoints. As in the case of FIG. 4, the system of the present invention, in one aspect, provides an estimate of the refractive index at terminal purity or the current contamination level by fitting a suitable curve to the refractive index data taken over a selected time period. Typically, the system discards spurious (high and low) measurements (data spikes), such as shown by numeral 412 (FIG. 4) and numeral 515 (FIG. 5) before fitting a curve for estimating terminal values.

Figure 6:
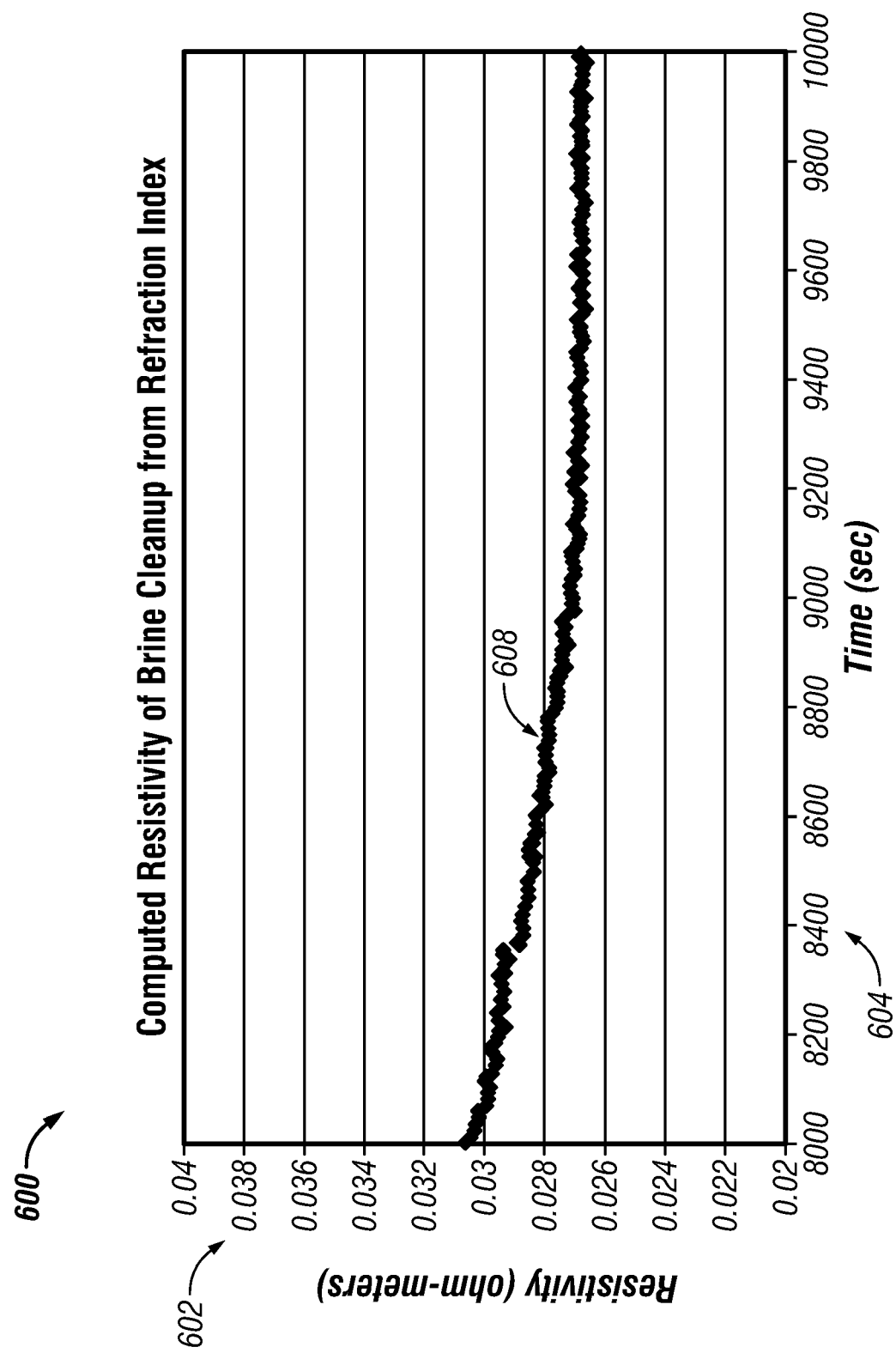
FIG. 6 is a graph showing an example of computed resistivity from refractive index.

Resistivity of the formation fluid is related to the refractive index of the fluid and thus can be calculated from the refractive index and used to estimate the terminal values. FIG. 6 is a graph 600 showing an example of computed resistivity from refractive index measured during clean-up. In the case where the drilling fluid is fresh water-based mud and the connate fluid is formation brine, the refractive index increases as the clean-up continues. This is because the density of the formation brine is typically greater than the water-based mud. However, the resistivity of the formation brine is less than the fresh water-based mud and thus will decrease as the clean up continues. FIG. 6 represents an example where the resistivity computed or calculated from the refractive index decreases as the clean up continues. The computed resistivity is shown plotted along the y-axis 602 and the time is shown plotted along the x-axis 604. The computed resistivity is shown from the pumping start time, which in this particular case is shown to be at 8000 seconds and continues to a time of 10,000 seconds. The time prior to the pumping start time relates to performing other functions with the downhole tool, such as setting the tool, etc. The resistivity values over time are shown by the arrow 608. As, noted above, the refractive index data or the computed resistivity data from the refractive index may be used to estimates the terminal purity or the contamination level by a suitably curve fitting such data. To compute the resistively from the refractive index shown in the example of graph 600, any known relationship may be used. Such relationships are known and this not described herein. The relationships are stored in the memory either downhole or at surface and are used to compute resistivity from the measured refractive index values.

The curve fitting may be done by a processor in the downhole tool or at the surface processor or a suitable combination thereof. In one aspect, the measured data, such as shown in FIGS. 4 and 5, or computed data, such as shown in FIG. 6 may be transmitted to a surface processor, where the processor using programmed instructions fits a curve for a certain number of data points and extrapolates the curve to determine the terminal purity or terminal contamination and the current purity or contamination levels. In another aspect, the programs may be stored in the memory downhole accessible to the downhole processor, wherein the downhole processor performs the curve fitting and provides the results to the surface via the telemetry system. As noted above, any suitable curve fitting method may be used to fit a curve to the refractive index measurements or the computed resistivity. Examples of certain curve fitting methods are provided below.

In one embodiment, the method and apparatus of the present invention fit the measurement data to a non-asymptotic curve. One example of a non-asymptotic curve is a curve that provides a fit to the data over a typical or selected pumping time, such as between 30 minutes to two hours, and then extrapolates the results to several times the pumping time, but which approaches plus or minus infinity at infinite times, such as a power series approximation.

In one aspect, present invention fits a continuously-differentiable, non-asymptotic curve to the raw data. The fit can be to the elapsed time or to the volume of the fluid pumped. The present invention may use, for example, but is not limited to, fitting to the raw data points a non-asymptotic curve such as $A(t)=c_1+c_2t^{1/2}+c_3t^{1/3}+c_4t^{1/4}$. Using calculus, the program analytically calculates the first derivative as $dA/dt=(c_2/2)t^{-1/2}+(c_3/3)\ t^{-2/3}+(c_4/4)t^{-3/4}$. For the purpose of using this method, $A_0$ is denoted to be the "terminal" refractive index, i.e. the refractive index at some very long time (e.g., 24 hours), which time is much longer than the time at which the pumping is normally terminated. As time progresses, both $(A_0-A)$ and $t(dA/dt)$ decrease, where A is the refractive index at time t. Assuming that both such values decrease at the same rate, then they are proportional to each other, which means $(A_0-A)=mt(dA/dt)$, where "m" is a constant. In one aspect, the present method tries various estimates for $A_0$ until it finds an estimated value of $A_0$ that produces an acceptable or the best linear, least-squares fit between $y=(A-A_0)$ and $x=[t(dA/dt)]$. The best fit is given by $y=mx+b$, where the intercept b is closest to zero, which has been determined to be more sensitive than finding the maximum "$R^2$" for linear fits between two variables that are directly proportional. To perform the curve fitting, the present invention selects a raw data point at a selected time, t, (which may be the latest time, t) at which the actual data intersects (or gets closest to) the best fit line. To forecast refractive index at a slightly later time, $t+\Delta t$, the method uses $\Delta A=(A_0-A)/[1+m(1+t/\Delta t)]$ which is obtained by replacing $dA/dt$ by $\Delta A/\Delta t$, replacing t by $t+\Delta t$, and replacing A by $A+\Delta A$ in $(A_0-A)=mt(dA/dt)$. The method then recursively applies this $\Delta A$ formula to forecast the refractive index at $t+\Delta t$ and then uses the newly-calculated refractive index to compute the refractive index at a slightly later time, $t+2\Delta t$, and so on, for all future times. In this manner the method generates future forecasts for $A(t)$.

In this method, if the slope m of the fit is positive, it indicates that an undesirable section of raw data has been selected, which is curving upward or downward towards plus or minus infinity. In such a case the method selects a new raw data point at some time, t, and continues the process of curve fitting, as described above. For data that is rising and leveling off over time, the fraction of terminal purity at any future time, t, is given by $A(t)/A_0$. For data that is falling and leveling off over time, the fraction of terminal purity at any future time, t, is given by $[A_S-A(t)]/[A_S-A_0]$, where $A_S$ is the starting refractive index at the left edge (the earliest time) of the selected data window.

Thus, in one aspect, the present disclosure provides a method for estimating a characteristic or parameter of interest, such as a current, future or terminal purity or contamination of brine in the formation fluid being withdrawn or pumped at a selected location in the wellbore during the withdrawal of the fluid. In one aspect, the method may is for estimating a characteristic of brine in a fluid obtained from a formation that has water-based mud invasion. The method may include estimating a refractive index of a connate brine from well log measurements; withdrawing the fluid from the formation; measuring a refractive index of the fluid a plurality of times during the withdrawal of the fluid from the formation; and comparing the estimated refractive index with a refractive index measured during the withdrawal of the formation fluid to estimate the characteristic of the brine. The characteristic or property of interest may be the contamination level in the fluid sample or the purity of the brine in the fluid sample or fraction of pure or connate brine or that of contamination in the fluid sample.

In another aspect, the method may estimate a characteristic of brine in a fluid obtained from a formation that has water-based mud invasion, wherein the method includes: estimating refractive index of connate brine from well log data, such as resistivity or other electrical logs; withdrawing the fluid from the formation; measuring refractive index of the fluid a plurality of times during the withdrawal of the fluid; fitting a curve to data values that correspond to the plurality of refractive index measurements; and estimating the characteristic of the brine from the estimated refractive index and the fitted curve. The method may further include estimating a terminal value of the data values and/or estimating a contamination level or purity level of the brine at a future time from the estimated refractive index and the fitted curve. The data values to which the curve is fitted may be the actual refractive index measured values or resistivity values that are derived from the measured refractive index values. In one aspect, the withdrawing of the fluid is terminated when the difference between the estimated refractive index and the terminal value is greater than a selected value. In another aspect, a formation fluid sample is collected when the purity of the brine is determined to be of an acceptable level. In another aspect, the estimated refractive index of connate brine is computed corresponding a selected temperature and pressure.

In another aspect, a method is provided for estimating a characteristic of a fluid during the withdrawal of the fluid from a formation, which method includes: withdrawing the fluid from a formation; measuring a refractive index of the fluid during the withdrawal of the formation fluid to obtain a plurality of refractive index values; obtaining a plurality of resistivity values corresponding to the plurality of refractive index values; fitting a curve through the plurality of resistivity values; estimating a terminal value of the resistivity values from the fitted curve; and estimating the characteristic of the fluid using a current resistivity value and the estimated terminal value. The characteristic of the fluid may be a terminal value of contamination in the fluid; terminal value of purity of the fluid; terminal value of a hydrocarbon content in the fluid; fraction of contamination in the fluid; fraction of oil in the fluid; fraction of gas in the fluid; or fraction of water in the fluid. Any of the methods may estimate components of the fluid and display a visual image of the estimated components that may be a gray scale visual image or a color visual image and each such image may be a two-dimensional or a three-dimensional image.

In another aspect, apparatus for estimating a characteristic of brine in a fluid withdrawn from a formation is disclosed that may include a: probe to withdraw the fluid from the formation; a refractometer that provides refractive index measurements of the fluid during the withdrawal of the fluid from the formation; a storage device that stores an estimated value of a refractive index of connate brine in the formation that is obtained using well log data; and a processor that estimates the characteristic of the brine from the estimated value of the refractive index of the connate brine and refractive index measurements made during the withdrawal of the fluid from the formation. A sample chamber may be used to collect a fluid sample. A pump may be used to pump the fluid from the formation into the sample chamber against hydrostatic pressure. Compressed gas in a chamber may be used to pressurize the fluid in the sample chamber. In another aspect, the processor may fit a curve to data values that correspond to the plurality of refractive index measurements and estimate the characteristic of the brine in the withdrawn fluid from the estimated refractive index of the connate brine and the fitted curve. The processor also may estimate a terminal value of the data values and estimate a contamination level or purity level of the brine in the withdrawn fluid at a future time from the estimated refractive index of the connate brine and the fitted curve. The data values used for fitting the curve may be the data values that correspond to measured values of the plurality of the refractive index measurements or resistivity values corresponding to the plurality of refractive index measurements. In another aspect, the processor may be configured to cause the taking of a sample of the fluid from the formation when a selected data value indicates that the purity level of brine or the contamination level in the brine is acceptable.

In another aspect, a computer-readable medium is provided that has embedded therein a computer program, which may include: a set of instructions to fit a curve to data corresponding a plurality of refractive index measurements of a fluid taken during withdrawal of the fluid from a formation; a set of instructions to estimate a terminal value of the refractive index from the fitted curve; and a set of instructions to estimate a characteristic of brine in the fluid from the fitted curve and an estimated value of connate brine computed from using well log data. The computer program may further include a set of instructions to fit the curve to the data values over a selected time and extrapolate the fitted curve to a multiple of the selected time that approaches plus or minus infinity at infinite time.

The computer-readable medium may be a ROM, RAM, CD ROM, DVD, FLASH or any other computer-readable medium, now known or unknown, that, when executed, causes a computer such as, for example, a processor in downhole controller 418 and/or a processor in surface controller 412, to implement the methods of the present invention.

The foregoing description is directed to particular embodiments of the present invention for the purpose of illustration and explanation. It will be apparent, however, to one skilled in the art that many modifications and changes to the embodiment set forth above are possible. It is intended that all such changes and modifications be interpreted as part of the disclosure.

What is claimed is:

1. A method of estimating a characteristic of brine in a fluid obtained from a formation that has water-based mud invasion, the method comprising:
   estimating a refractive index of a connate brine using in part well log data;
   withdrawing the fluid from the formation;
   measuring a refractive index of the fluid a plurality of times during the withdrawal of the fluid from the formation; and
   estimating the characteristic of the brine using the estimated refractive index and the refractive index measured during the withdrawal of the formation fluid.

2. The method of claim 1, wherein the well log data is one of: (i) resistivity; (ii) porosity; and (iii) neutron cross section.

3. A method of estimating a characteristic of brine in a fluid obtained from a formation that has water-based mud invasion, the method comprising:
   estimating a refractive index of a connate brine from well log measurements;
   withdrawing the fluid from the formation;
   measuring a refractive index of the fluid a plurality of times during the withdrawal of the fluid;
   fitting a curve to data values that correspond to the plurality of refractive index measurements; and
   estimating the characteristic of the brine from the estimated refractive index and the fitted curve.

4. The method of claim 3 further comprising estimating a terminal value of the data values.

5. The method of claim 4 further comprising estimating a contamination level or a purity level of the brine at a future time from the estimated refractive index and the fitted curve.

6. The method of claim 3, wherein the data values correspond to one of: values of the plurality of the refractive index measurements; and resistivity values corresponding to the plurality of refractive index measurements.

7. The method of claim 3, wherein estimating the refractive index comprises estimating the refractive index corresponding to a selected temperature and pressure.

8. A method of estimating a characteristic of a fluid, comprising:
   withdrawing the fluid from a formation;
   measuring a refractive index of the fluid during the withdrawal of the formation fluid to obtain a plurality of refractive index values;
   obtaining a plurality of resistivity values corresponding to the plurality of refractive index values;
   fitting a curve through the plurality of resistivity values;
   estimating a terminal value of the resistivity values from the fitted curve; and
   estimating the characteristic of the fluid using a current resistivity value and the estimated terminal value.

9. The method of claim 8, wherein the characteristic of the fluid is one of a: terminal value of contamination in the fluid; terminal value of purity of the fluid; terminal value of a hydrocarbon content in the fluid; fraction of contamination in the fluid; fraction of oil in the fluid; fraction of gas in the fluid; and fraction of water in the fluid.

10. The method of claim 8 further comprising estimating components of the fluid and displaying a visual image of the estimated component as one of: (i) a gray scale visual image; and (ii) a color visual image.

11. The method of claim 8, wherein fitting a curve comprises one of: fitting an asymptotic curve; fitting a non-asymptotic curve; and fitting a least square fit curve.

12. An apparatus for estimating a characteristic of brine in a fluid withdrawn from a formation, comprising:
   a probe to withdraw the fluid from the formation;
   a refractometer that provides refractive index measurements of the fluid during the withdrawal of the fluid from the formation; and
   a storage device that has stored therein an estimated value of refractive index of connate brine in the formation that is obtained using well log data; and
   a processor that estimates the characteristic of the brine from the estimated value of the refractive index of the connate brine and the refractive index measurements made during the withdrawal of the fluid from the formation.

13. The apparatus of claim 12 further comprising a chamber that collects fluid and a pump that pumps fluid in the chamber.

14. The apparatus of claim 12, wherein the characteristic is one of contamination in the brine and purity of the brine in the fluid being withdrawn from the formation.

15. An apparatus for estimating a characteristic of brine obtained from a formation that has water-based mud invasion, comprising:
   a probe to withdraw a fluid from the formation;
   a refractometer that provides a plurality of refractive index measurements of the fluid during the withdrawal of the fluid from the formation;
   a storage device that has stored therein an estimated value of refractive index obtained from well log data; and
   a processor that:
      fits a curve to data values that correspond to the plurality of refractive index measurements; and
      estimates the characteristic of the brine in the withdrawn fluid from the estimated refractive index and the fitted curve.

16. The apparatus of claim 15, wherein the processor further estimates a terminal value of the data values.

17. The apparatus of claim 15, wherein the processor further estimates a contamination level or a purity level of the brine in the withdrawn fluid at a future time from the estimated refractive index and the fitted curve.

18. The apparatus of claim 15, wherein the data values correspond to one of: the measured values of the plurality of the refractive index measurements; and resistivity values corresponding to the plurality of refractive index measurements.

19. The apparatus of claim 15 further comprising a pump that pumps the fluid from the formation into a chamber or the wellbore.

20. The apparatus of claim 15, wherein the processor causes taking of a sample of the fluid from the formation when a selected data value indicates one of: (i) an acceptable purity level of the brine, and (ii) an acceptable contamination level in the brine.

21. The apparatus of claim 15 further comprising a conveying member that is one of a wireline and tubing that conveys the probe and the refractometer to a downhole location.

22. The apparatus of claim 15, wherein the processor processes the plurality of refractive index measurements at one of: downhole; the surface; and partially downhole and partially at the surface.

23. The apparatus of claim 15 further comprising a chamber for collecting the fluid from the formation therein under a condition that is one of: the withdrawn fluid is pumped into the chamber at a pressure that is above a hydrostatic pressure; and where a gas chamber associated with the chamber increases pressure on the fluid in the chamber.

24. A computer-readable medium containing a computer program accessible to a processor that executes instructions contained in the computer program, wherein the computer program comprises:
   a set of instructions to fit a curve to data corresponding to a plurality of refractive index measurements of a fluid taken during withdrawal of the fluid from a formation;
   a set of instructions to estimate a terminal value of the refractive index from the fitted curve; and
   a set of instructions to estimate a characteristic of brine in the fluid from the fitted curve and an estimated value of connate brine computed using well log data.

25. The computer-readable medium of claim 24, wherein the computer program further comprises a set of instructions to fit the curve to the data values over a selected time and extrapolate the fitted curve to a multiple of the selected time that approaches plus or minus infinity at infinite time.

* * * * *